United States Patent
Kishi et al.

(10) Patent No.: US 10,443,772 B2
(45) Date of Patent: Oct. 15, 2019

(54) PIPE JOINT STRUCTURE, SEAL MEMBER, ASSEMBLED CONDITION MANAGEMENT METHOD FOR PIPE JOINT, AND ASSEMBLED CONDITION MANAGEMENT DEVICE FOR PIPE JOINT

(71) Applicant: KUBOTA CORPORATION, Osaka-shi, Osaka (JP)

(72) Inventors: Shozo Kishi, Amagasaki (JP); Takaaki Kagawa, Amagasaki (JP); Keita Oda, Amagasaki (JP); Yuito Komaru, Amagasaki (JP)

(73) Assignee: KUBOTA CORPORATION, Osaka (JP)

( * ) Notice: Subject to any disclaimer, the term of this patent is extended or adjusted under 35 U.S.C. 154(b) by 617 days.

(21) Appl. No.: 15/028,539

(22) PCT Filed: Sep. 29, 2014

(86) PCT No.: PCT/JP2014/075850
§ 371 (c)(1),
(2) Date: Apr. 11, 2016

(87) PCT Pub. No.: WO2015/053117
PCT Pub. Date: Apr. 16, 2015

(65) Prior Publication Data
US 2016/0290540 A1 Oct. 6, 2016

(30) Foreign Application Priority Data
Oct. 9, 2013 (JP) .................. 2013-211833

(51) Int. Cl.
*F16L 1/09* (2006.01)
*F16L 37/088* (2006.01)
(Continued)

(52) U.S. Cl.
CPC .............. *F16L 37/088* (2013.01); *E03F 3/06* (2013.01); *F16J 15/064* (2013.01); *F16L 1/09* (2013.01);
(Continued)

(58) Field of Classification Search
CPC ......... F16L 2201/00; F16L 1/09; F16L 21/02; F16L 21/03
(Continued)

(56) References Cited

U.S. PATENT DOCUMENTS 3,281,929 A * 11/1966 Shinnick .................. F16L 1/09
29/237
3,325,174 A * 6/1967 Weaver .................. F16L 21/03
277/604
(Continued)

FOREIGN PATENT DOCUMENTS

DE       101 44 552 A1    2/2004
JP       S54-23218 A      2/1979
(Continued)

OTHER PUBLICATIONS

Dec. 22, 2014 International Search Report issued in International Patent Application No. PCT/JP2014/075850.
Sep. 26, 2017 Office Action issued in Japanese Patent Application No. 2013-211833.
Partial Translation of Jun. 28, 2017 Office Action issued in Taiwanese Patent Application No. 103134259.
(Continued)

*Primary Examiner* — David Bochna
(74) *Attorney, Agent, or Firm* — Oliff PLC

(57) ABSTRACT

A pipe joint structure provided with: a heel section configured so that a spigot formed on the end section of a pipe is inserted via a seal member into a socket formed in the end section of another pipe and seal member is fitted to a recessed section formed on the inner circumferential section of the socket; and a valve section compressed between the inner circumferential surface of the socket and the outer circumferential surface of the spigot. Additionally, a marker
(Continued)

member is provided to the heel section that is accommodated in the recessed section. The socket circumference section of the pipe joint structure is subjected to non-contact inspection by a marker detection device from the spigot-side pipe along the axial direction of the pipe and the quality of the joining state of the pipe joint structure is determined on the basis of whether the marker member is detected.

4 Claims, 11 Drawing Sheets

(51) Int. Cl.
  *E03F 3/06* (2006.01)
  *F16L 1/10* (2006.01)
  *F16L 21/08* (2006.01)
  *F16J 15/06* (2006.01)
  *G01N 21/95* (2006.01)

(52) U.S. Cl.
  CPC .............. *F16L 1/10* (2013.01); *F16L 21/08* (2013.01); *G01N 21/95* (2013.01); *F16L 2201/10* (2013.01); *F16L 2201/60* (2013.01)

(58) Field of Classification Search
  USPC .......................................... 285/93
  See application file for complete search history.

(56) References Cited

U.S. PATENT DOCUMENTS

| | | | |
|---|---|---|---|
| 4,039,087 A * | 8/1977 | Sandvick, Sr. | ........... F16L 1/09 29/237 |
| 4,205,424 A | 6/1980 | Nagao et al. | |
| 4,502,407 A * | 3/1985 | Stevens | ............... E02B 17/0034 114/222 |
| 4,519,122 A * | 5/1985 | Miller | ....................... F16L 1/09 29/237 |
| 2002/0106923 A1 | 8/2002 | Copeland et al. | |
| 2010/0289256 A1 * | 11/2010 | Shumard | ................. F16L 21/03 285/18 |
| 2010/0330349 A1 | 12/2010 | Ewald et al. | |

FOREIGN PATENT DOCUMENTS

| | | |
|---|---|---|
| JP | H05-231570 A | 9/1993 |
| JP | 2000-234684 A | 8/2000 |
| JP | 2003-14173 A | 1/2003 |
| JP | 2013-014173 A | 1/2013 |

OTHER PUBLICATIONS

May 12, 2017 Supplementary Partial Search Report issued in European Patent Application No. 14852285.7.
Jul. 13, 2018 Office Action issued in European Patent Application No. 14852285.7.
Feb. 12, 2019 Office Action issued in Indian Patent Application No. 201627008061.

* cited by examiner

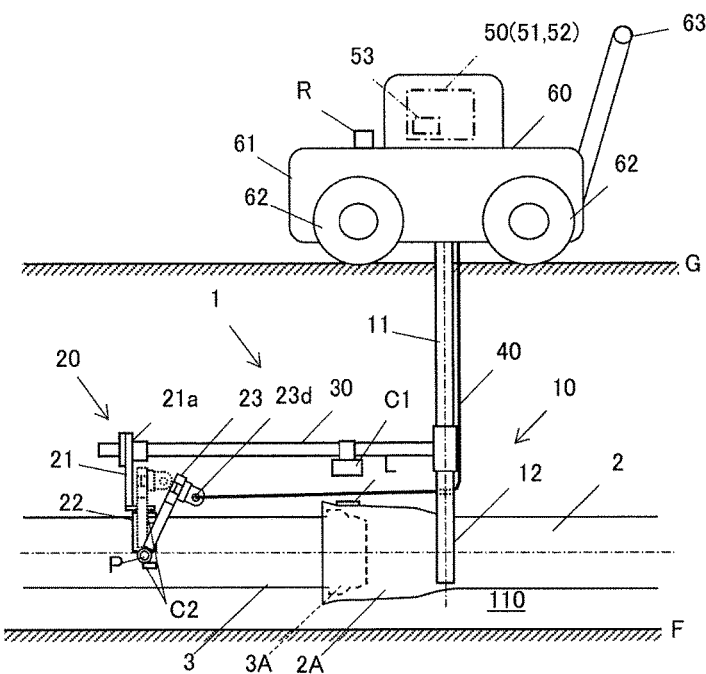
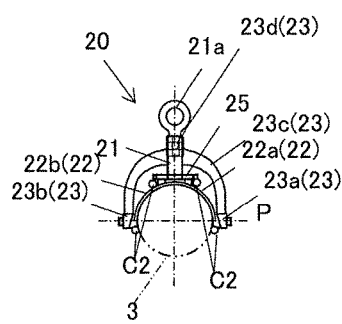
Fig.1B
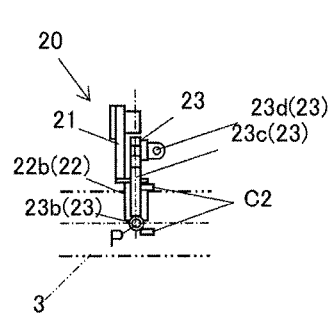
Fig.1C
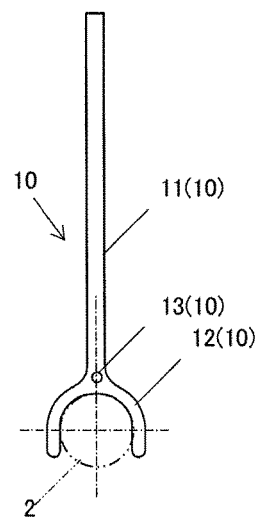
Fig.1D
Fig.1A

PIPE JOINT STRUCTURE, SEAL MEMBER, ASSEMBLED CONDITION MANAGEMENT METHOD FOR PIPE JOINT, AND ASSEMBLED CONDITION MANAGEMENT DEVICE FOR PIPE JOINT

TECHNICAL FIELD

The present invention relates to a pipe joint structure, a seal member used for a pipe joint, an assembled condition management method for the pipe joint, and an assembled condition management device for the pipe joint, and particularly relates to a pipe joint structure including a seal member in which a heel section is fitted to a recessed section that is formed in an inner circumferential section of a socket and a bulb section is compressed between the inner circumferential surface of the socket and an outer circumferential surface of a spigot, the seal member used for a pipe joint, an assembled condition management method for the pipe joint, and an assembled condition management device for the pipe joint.

BACKGROUND ART

Ductile cast iron pipes, widely used for water supply and sewer pipes, employ what is known as a push-on type pipe joint structure.

For example, Patent Literature 1 discloses a pipe joint structure having the following configuration. Specifically, into a socket that is formed at an end of one pipe, a spigot that is formed at an end of another pipe is inserted. A sealing rubber ring is disposed in a compressed manner between an inner circumferential surface of the socket and an outer circumferential surface of the spigot. A lock ring provided on an inner circumferential groove portion of the socket engages with a protrusion formed on the spigot, so that the pipe is prevented from being pulled out of the other pipe.

Patent Literature 2 discloses the following configuration. Specifically, whether pipes are assembled with a rubber ring in an appropriate position is determined by measuring a distance between a pipe end of the socket and a position to be in contact with the rubber ring with a feeler gauge, or by inserting a dedicated assembling checker from the pipe end of the socket to the position to be in contact with the rubber ring.

PRIOR ART DOCUMENTS

Patent Documents

[PTL1] Japanese Unexamined Patent Application Publication No. 2004-340228
[PTL2] Japanese Unexamined Patent Application Publication No. 2012-123589

SUMMARY OF INVENTION

Problems to be Solved by the Invention

As illustrated in FIG. 11(a), when the iron pipes, employing the push-on type joint structure as described above, are assembled, the following operation needs to be performed. Specifically, in a state where a socket 104 of one pipe T1 is receiving a spigot of another pipe T2, an assembling device 100, formed of a sling belt or a chain, is wound around the socket-side pipe T1 at a portion adjacent to the socket 104, a similar assembling device 101 is wound around the spigot-side pipe T2 at a portion adjacent to the spigot, and the assembling devices 100 and 101 are wound up through a manual operation with lever hoists 102 and 103 disposed on both sides of the pipes T1 and T2 and between the assembling devices.

After the assembling operation is completed, whether the rubber ring is appropriately positioned is checked by using the feeler gauge or the assembling checker described above.

Accordingly, a plurality of operators need to enter a trench 110 excavated for laying the pipes T1 and T2 as illustrated with a dotted line in FIG. 11(b), and perform the assembling operation that is extremely cumbersome. Thus, the trench 110 excavated needs to have a width sufficiently larger than a pipe diameter.

In view of the problems described above, an object of the present invention is to provide a pipe joint structure, a seal member used for a pipe joint, an assembled condition management method for the pipe joint, and an assembled condition management device for the pipe joint, with which an operator can easily check whether a joining operation for pipes has been appropriately completed without entering a trench.

Means for Solving the Problems

To achieve the object described above, a first characteristic configuration of a pipe joint structure according to the present invention is, as set forth in claim 1: a pipe joint structure in which a spigot that is formed at an end of one pipe to be joined is inserted into a socket that is formed at an end of another pipe, and a seal member is provided between the socket and the spigot, in which the seal member includes a heel section fitted to a recessed section formed in an inner circumferential section of the socket; and a bulb section compressed between an inner circumferential surface of the socket and an outer circumferential surface of the spigot, the heel section that is accommodated in the recessed section being provided with a marker member that is detectable in a non-contact manner from a side of the spigot along a pipe axial direction.

When the spigot-side pipe is appropriately inserted into the socket, a state where the heel section of the seal member is fitted to the recessed section is maintained, and thus the marker member, provided to the heel section, will not be observed from the external. When the spigot-side pipe being inserted to the socket is pulled by the spigot so that at least a part of the heel section is separated from the seal member accommodating recessed section, the marker member, provided to the heel section, is observed from the external. Thus, whether the assembled condition is appropriate can be easily determined.

A second characteristic configuration of the pipe joint structure according to the present invention is, as set forth in claim 2: the marker member includes a colored member having a color different from a color of the seal member, in addition to the first characteristic configuration described above.

The marker member includes the colored member having a color different from a color of the seal member. Thus, the heel section can be extremely easily distinguished from the marker member.

A characteristic configuration of a seal member according to the present invention is, as set forth in claim 3: a seal member used for the pipe joint structure of the first or second characteristic configuration, in which the heel section that is fitted to the recessed section that is formed in the inner circumferential section of the socket is provided with a marker member with which whether the heel section is separated from the recessed section is able to be detected.

Whether the heel section is appropriately accommodated in the recessed section can be easily determined based on whether the marker member is observed.

A first characteristic configuration of an assembled condition management method for a pipe joint according to the present invention is, as set forth in claim 4: an assembled condition management method for a pipe joint in which a spigot that is formed at an end of one pipe to be joined is inserted into a socket that is formed at an end of another pipe, and a seal member is provided between the socket and the spigot, the seal member including: a heel section that is fitted to a recessed section formed in an inner circumferential section of the socket; and a bulb section that is compressed between an inner circumferential surface of the socket and an outer circumferential surface of the spigot, the heel section that is accommodated in the recessed section being provided with a marker member, the method including: checking the marker member in a non-contact manner from a side of the spigot along a pipe axial direction in a state where the pipe joint is assembled.

When the spigot-side pipe being inserted to the socket is pulled by the spigot so that at least a part of the heel section is separated from the recessed section, whether the marker member is observed is determined in a non-contact manner. When the seal member is appropriately accommodated in the recessed section, the marker member will not be observed. Thus, an operator needs not to enter the trench and use a feeler gauge to inspect a circumferential section of the socket in detail, and the inspection can be performed extremely easily.

A first characteristic configuration of an assembled condition management device for a pipe joint according to the present invention is, as set forth in claim 5: an assembled condition management device for a pipe joint in which a spigot that is formed at an end of one pipe to be joined is inserted into a socket that is formed at an end of another pipe, and a seal member is provided between the socket and the spigot, in which the seal member includes: a heel section that is fitted to a recessed section formed in an inner circumferential section of the socket; and a bulb section that is compressed between an inner circumferential surface of the socket and an outer circumferential surface of the spigot, the heel section accommodated in the recessed section being provided with a marker member, and for the seal member, the assembled condition management device includes: a marker detection device that, in a state where the pipe joint is assembled, detects the marker member from the spigot-side pipe along an axial direction of the pipe in a non-contact manner.

In the state where the spigot-side contact piece is in contact with the spigot-side pipe, the marker detection device, attached to the spigot-side contact piece, determines whether the marker member is observed in a non-contact manner from the spigot-side pipe along the pipe axial direction. It can be determined that the heel section is separated from the recessed section when the marker member is observed by the marker detection device. It can be determined that the heel section appropriately accommodated in the recessed section when the marker member is not observed by the marker detection device.

A second characteristic configuration of the assembled condition management device for a pipe joint according to the present invention is, as set forth in claim 6: the marker member is a colored member having a color different from a color of the seal member, and the marker detection device includes an image capturing device with which whether there is the colored member is able to be determined with an image, in addition to the first characteristic configuration.

An image of the socket opening section side is captured from an end section of the socket-side pipe by the image capturing device attached to the spigot-side contact piece. It can be determined that the heel section is pulled by the spigot to be separated from the seal member accommodating recessed section, when the colored member having a color different from a color of the seal member is found in the image thus captured.

A third characteristic configuration of the assembled condition management device for a pipe joint according to the present invention is, as set forth in claim 7: a plurality of the image capturing devices are attached to the spigot-side contact piece at a predetermined interval, in addition to the second characteristic configuration.

With the plurality of image capturing devices attached to the spigot-side contact piece at an interval, an image of substantially the entire area along the socket can be captured by a single image capturing.

A fourth characteristic configuration of the assembled condition management device for a pipe joint according to the present invention is, as set forth in claim 8: the image capturing device is attached to the spigot-side contact piece via a movement mechanism that moves along the spigot-side outer circumferential surface, in addition to the second characteristic configuration.

With the image capturing device configured to move along the spigot-side outer circumferential surface via the movement mechanism, an image of substantially the entire area along the socket can be captured with a single image capturing device.

A fifth characteristic configuration of the assembled condition management device for a pipe joint according to the present invention is, as set forth in claim 9: the spigot-side contact piece is combined in the pipe joint assembling device that is remotely operated to automatically insert a spigot that is formed at an end of one pipe into a socket that is formed at an end of another pipe; the pipe joint assembling device includes: a socket-side supporting member that comes into contact with a socket-side pipe; a spigot-side supporting member including: a spigot-side contact piece that comes into contact with a spigot-side pipe; and a pivoting mechanism that pivots about a pivot axis, orthogonal to a pipe axis, so that the spigot-side contact piece is pressed and clamps the pipe; a guide shaft that is arranged in parallel with the pipe axis, and has one end fixed to the socket-side supporting member and another end to which the spigot-side supporting member is slidably connected; and a pulling operation member that performs an operation of making the pivoting mechanism pivot so that the pipe is clamped by the spigot-side contact piece pressed, is connected to the pivoting mechanism via the socket-side supporting member, and pulls the spigot in a clamped state toward a socket, in addition to any of the first to fourth characteristic configurations.

In the configuration described above, the socket-side supporting member is brought into contact with pipes, disposed on a trench bottom with a socket of one of the pipes receiving a spigot of the other one of the pipes, to be fit on a pipe circumferential surface, and a spigot-side contact piece of the spigot-side supporting member is brought into contact with the pipe circumferential surface to be fit on the pipe circumferential surface. In this state, the pulling operation member is operated to perform pulling, the pivoting mechanism pivots about a pivot axis, so that the spigot-side contact piece clamps the pipe.

In this state, when the pulling operation member is further operated to perform the pulling, the spigot-side pipe, clamped by the spigot-side contact piece is pulled toward a socket-side pipe, whereby the pipes are assembled. The spigot-side pipe is pulled toward the socket-side pipe, with the spigot-side supporting member sliding along the guide shaft, fixed to have the parallel position with respect to the axis of the socket-side pipe. Thus, the spigot-side pipe is prevented from inclining upward, whereby the pipes are assembled with the inclination of the axes thereof kept within a predetermined allowable angle (within a range of about ±4° for example). In the state where the pipes are assembled, the marker detection device, attached to the spigot-side contact piece, determines whether the marker of the seal member is observed.

With such a pipe joint assembling device, for example, the assembling operation can be completed only by operating the pulling operation member when the socket-side contact piece and the spigot-side contact piece moved downward from above the pipes disposed on the trench bottom can each be in contact with and fit on the pipe circumferential surface. Thus, the operator needs not to enter the trench and perform an operation of checking the condition of the seal member, and thus the trench excavated can have a small width.

Effects of Invention

As described above, the present invention can provide a pipe joint structure, a seal member used for a pipe joint, an assembled condition management method for the pipe joint, and an assembled condition management device for the pipe joint, with which an operator can easily check whether an assembling operation for pipes has been appropriately completed without entering a trench.

BRIEF DESCRIPTION OF DRAWINGS

FIG. 1(a) is a diagram illustrating an entire configuration of a pipe joint assembling device, FIG. 1(b) is a front view of a spigot-side supporting member, FIG. 1(c) is a side view of the spigot-side supporting member, and FIG. 1(d) is a front view of a socket-side supporting member.

EMBODIMENTS FOR CARRYING OUT THE INVENTION

Figure 2A:
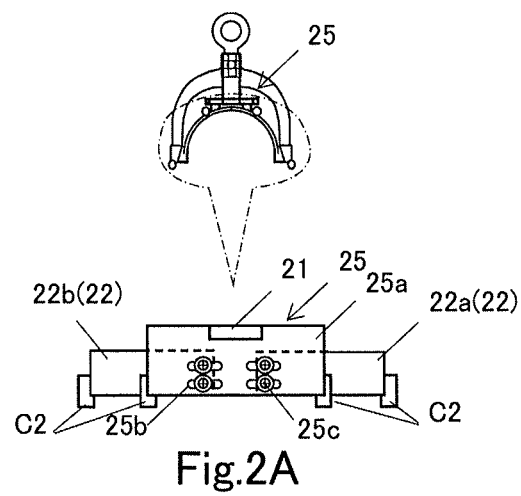
FIGS. 2(a) and 2(b) are diagrams illustrating a spigot-side contact piece and a coupling mechanism provided to the spigot-side supporting member.

A pipe joint structure, a seal member used for a pipe joint, an assembled condition management method for the pipe joint, and an assembled condition management device for the pipe joint according to the present invention are described below by using a pipe assembling operation for water supply pipes using ductile cast iron pipes (hereinafter, referred to as "iron pipes") as an example.

First of all, a pipe joint assembling device including the assembled condition management device for the pipe joint will be described. The present invention can be widely applied to pipeline construction for sewer pipes and the like, in addition to pipeline construction for the water supply pipes. The pipe joint assembling device described below is particularly suitable for assembling iron pipes, and can also be used for assembling other pipes such as resin pipes.

FIG. 1(a) illustrates a state where pipes 2 and 3, laid on a trench bottom F of a trench 110 formed by excavation on a ground surface G, are assembled with a pipe joint assembling device 1. The pipes 2 and 3 each have a socket formed on one end side and a spigot formed on the other end side.

The pipe joint assembling device 1 includes a socket-side supporting member 10, a spigot-side supporting member 20, a guide shaft 30, a pulling operation member 40, a supporting mechanism 50, and a moving member 60.

The socket-side supporting member 10 includes: a socket-side supporting shaft 11, in a vertical position, having a base end side supported by the supporting mechanism 50 in such a manner as to be vertically movable; and a socket-side contact piece 12 that is integrally formed on a distal end side of the socket-side supporting shaft 11 and comes into contact with a portion, adjacent to a socket 2A of the one pipe 2, from above in such a manner as to fit on a pipe circumferential surface.

As illustrated in FIG. 1(d), the socket-side contact piece 12 has a recessed section having a radius that is similar to or slightly smaller than a radius of the circumferential surface of the pipe 2, and comes into contact with the pipe circumferential surface by being moved downward from an upper side of the pipe 2. The socket-side supporting shaft 11 and the socket-side contact piece 12 are each made of a steel material. A hole section in FIG. 1(d) denoted by a reference numeral 13, is an insertion hole for a pulling wire 40 described later.

As illustrated in FIGS. 1(a), 1(b), and 1(c), the spigot-side supporting member 20 includes: a spigot-side supporting shaft 21 in the vertical position; a spigot-side contact piece 22 that comes into contact with a portion of the other pipe 3, adjacent to the spigot 3A, from above to be fit on a pipe circumferential surface; and a pivoting mechanism 23 that pivots about a pivot axis P, orthogonal to an axis of the pipe 3, to press the spigot-side contact piece 22 so that the pipe is clamped.

For example, the spigot-side supporting shaft 21 and the spigot-side contact piece 22 may be formed of a material other than the steel material, such as metal including an aluminum alloy and the like, or resin, and is preferably provided with a cushioning material, such as rubber or resin, at a portion to be in contact with the pipe so that the pipe surface is prevented from being damaged. For example, the pivoting mechanism 23 may also be formed of a material other than the steel material, such as metal including an aluminum alloy.

Four second image capturing devices C2 are attached on the spigot-side contact piece 22 at an interval. The second image capturing devices C2 are used for capturing an image of the socket after the pipes 2 and 3 are assembled.

The guide shaft 30 has a base end side fixed to a sleeve of the socket-side supporting member 10 in such a manner as to be in a parallel position with respect to an axis of the one pipe 2. The spigot-side supporting member 20 is slidably fit to the guide shaft 30. A first image capturing device C1 is attached to the guide shaft 30. This first image capturing device C1, described in detail later, is used for capturing an image of a trench and a pipe information label L attached to the socket-side pipe 2 from above before the pipes are assembled, and for capturing an image of the assembled portion from above after the pipes are assembled.

In the present embodiment, a QR code (registered trademark), indicating two-dimensional code information, is used as the pipe information label L. A form of the code information is not particularly limited, and known code information, such as a barcode, may be used as appropriate. Instead of the configuration where the pipe information label L is attached, a configuration may be employed in which the code information is carved or painted by using a paint on an outer surface of the pipe.

When the spigot-side pipe is a bend or a tee pipe, a portion of the pipe circumferential surface to be the upper surface when the socket on the other end is assembled, might differ each time the construction is performed. Thus, an annular member that is a thin film on which the pipe information label L is attached is fitted to the spigot-side pipe. Then, when the socket of the spigot-side pipe is assembled, an operation of rotating the annular member is performed so that the pipe information label L is positioned on the upper surface, whereby the image of the pipe information label L can be captured from above.

The pulling operation member 40 includes a pulling wire (hereinafter, denoted with a reference numeral "40") for performing an operation of making the pivoting mechanism 23 pivot from a side of the socket-side supporting member 10 so that the pipe 3 is clamped by the spigot-side contact piece 22, and pulling the spigot 3A toward the socket 2A in the clamped state. The socket-side supporting member 10, the spigot-side supporting member 20, the guide shaft 30, and the pulling operation member 40 form an assembling processing unit.

The supporting mechanism 50 is mounted to the moving member 60, and includes an electric elevation mechanism 51 that performs an operation of moving the socket-side supporting shaft 11 vertically with a rack and pinion mechanism and the like and an electric winch mechanism 52 that wounds up the pulling wire 40.

An operation switch for implementing the operation of moving the socket-side supporting shaft 11 vertically, and an operation switch for operating the winch mechanism 52 are provided adjacent to the supporting mechanism 50. Furthermore, a depth of cover calculating unit 53 that measures a distance of vertical movement of the assembling processing unit caused by the elevation mechanism 51 to calculate the depth of cover is further provided.

The moving member 60 includes a vehicle body 61 on which the supporting mechanism 50 is mounted and a pair of front and rear wheels 62 on both sides of the excavated trench 110. The wheels 62 movably support the vehicle body 61.

A GPS receiver R, receiving GPS electrical waves for identifying a current location of the moving member 60, is mounted to the moving member 60. In the present embodiment, an example is described where the moving member 60 is moved by manually pulling or performing the other like operation on an operation handle 63. Alternatively, the moving member may be provided with a driver to be of a self-traveling type.

The guide shaft 30 is fitted to a top section of the spigot-side supporting shaft 21 via a bearing 21a so that the spigot-side supporting member 20 can slide along the guide shaft 30. A pair of spigot-side contact pieces 22 (22a, 22b) are bolted to a lower end section of the spigot-side supporting shaft 21 via a coupling mechanism 25.

Figure 2B:
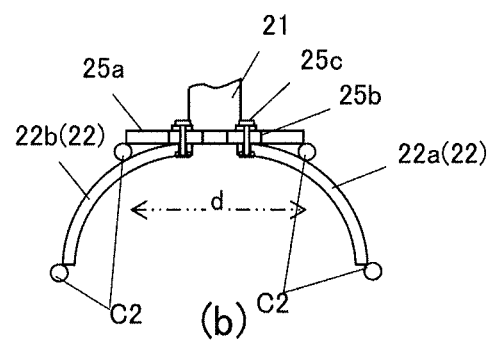

More specifically, as illustrated in FIGS. 2(a) and 2(b), the spigot-side contact piece 22 includes two left and right wide curved plates 22a and 22b that are coupled to a coupling plate 25a with bolts 25c. Long holes 25b, with which a relative distance d between the curved plates 22a and 22b along the circumferential surface of the pipe 3 can be adjusted, are formed on the coupling plate 25a. The coupling plate 25a on which the long holes 25b are formed and the bolts 25c form the coupling mechanism 25.

The coupling is achieved via the coupling mechanism 25 with the relative distance d between the two left and right curved plates 22a and 22b being adjustable. Thus, when the spigot-side contact piece 22 is brought into contact with the upper surface of the pipe 3, the relative distance d between the two left and right curved plates 22a and 22b can be adjusted to be long to ensure the contact. When pressing force generated by the operation of making the pivoting mechanism 23 pivot is applied in this state, the relative distance d between the two left and right curved plates 22a and 22b is quickly reduced, whereby the pipe 3 can be smoothly clamped by the spigot-side contact piece 22.

Figure 10A:
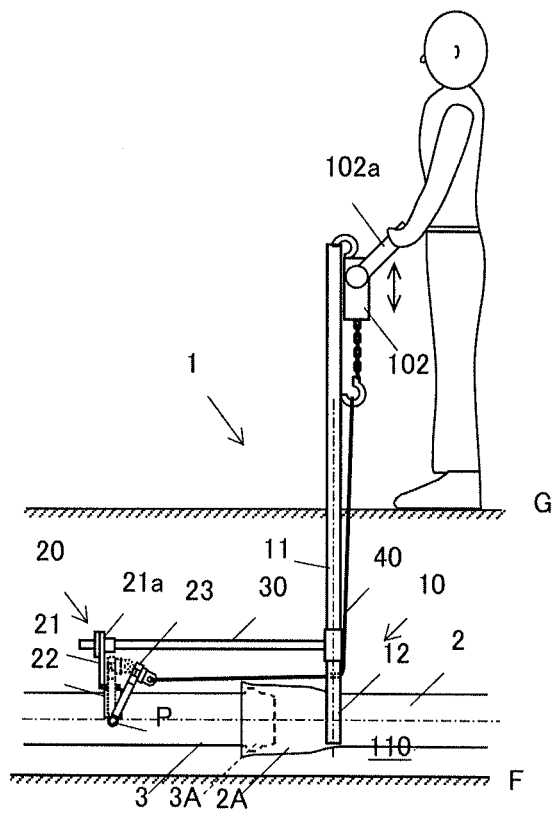
FIG. 10(a) is a diagram illustrating a pipe joint assembling device according to another embodiment.
Figure 10B:
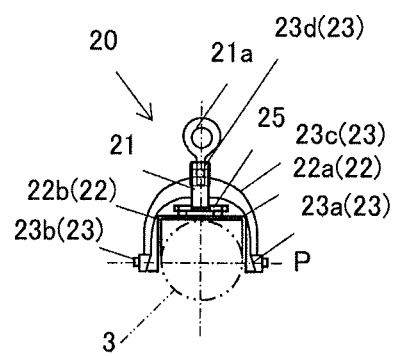
FIG. 10(b) is a front view of a spigot-side supporting member according to the other embodiment.

In the example described above, the spigot-side contact piece 22 includes the two left and right curved plates 22a and 22b, coupled to each other via the coupling plate 25a. The spigot-side contact piece 22 may come into contact with at least three points including the top section and the left and right side sections opposite to each other along the circumferential surface of the pipe 3. For example, two left and right pieces each having a "V" shape may be coupled to each other via the coupling plate 25a so that a "rectangular U" shape with a lower side open is formed as illustrated in FIG. 10(b).

When the spigot-side contact piece 22 is formed of a material such as resin to be elastically deformable, the spigot-side contact piece 22 may be formed as a single body with no coupling plate 25a. Furthermore, the spigot-side contact piece 22 may include three members including: the two left and the right pieces that have a "V shape", come into contact with the left and the right side portions of the pipe 3 opposite to each other, and are coupled to each other via the coupling plate 25a to form the rectangular U shape with a lower side open as described above; and a top section contact piece that is provided on a center portion of the two left and the right pieces, and comes into contact with an upper section of the pipe 3.

A plurality of the spigot-side contact pieces 22, corresponding to a nominal diameter, are prepared in advance, and are detachably attached to the spigot-side supporting shaft 21. Similarly, the socket-side supporting shaft 11 on which a plurality of the socket-side contact pieces 12, corresponding to the nominal diameter, are attached in advance is prepared.

FIG. 1(*d*) illustrates an example where the socket-side contact piece 12 and the socket-side supporting shaft 11 are integrally formed. The plurality of socket-side contact pieces 12, corresponding to the nominal diameter, may be detachably attached to the socket-side supporting shaft 11. The socket-side contact piece 12 may also be in contact with at least three points including the top section and the left and the right side sections opposite to each other along the circumferential surface of the pipe 2, and thus may form a "rectangular U" shape with a lower side open for example.

Referring back to FIGS. 1(*a*), 1(*b*), and 1(*c*), the pivoting mechanism 23 includes: an arch-shaped member 23*c* serving as a pivoting member and having both end sections 23*a* and 23*b* positioned on the pivot axis P to clamp the pipe 3 from the sides; and an annular member 23*d* rotatably attached to a top section of the arch-shaped member 23*c*. The puling wire 40 has an end section fixed to the annular member 23*d*.

A cam mechanism 24 is disposed between the both end sections 23*a* and 23*b* of the arch-shaped member 23*c* and between both end sections of the curved plates 22*a* and 22*b*. The cam mechanism 24 has a pair of cam members 24*a* and 24*b* disposed to be relatively rotatable with each other about a common axis with inclined cam surfaces 24*c*, inclined in opposite directions, facing each other. One cam member 24*a* is attached to the curved plates 22*a* and 22*b*, and the other cam member 24*b* is attached to the both end sections 23*a* and 23*b* of the arch-shaped member 23*c*.

Figures 3A, 3B:
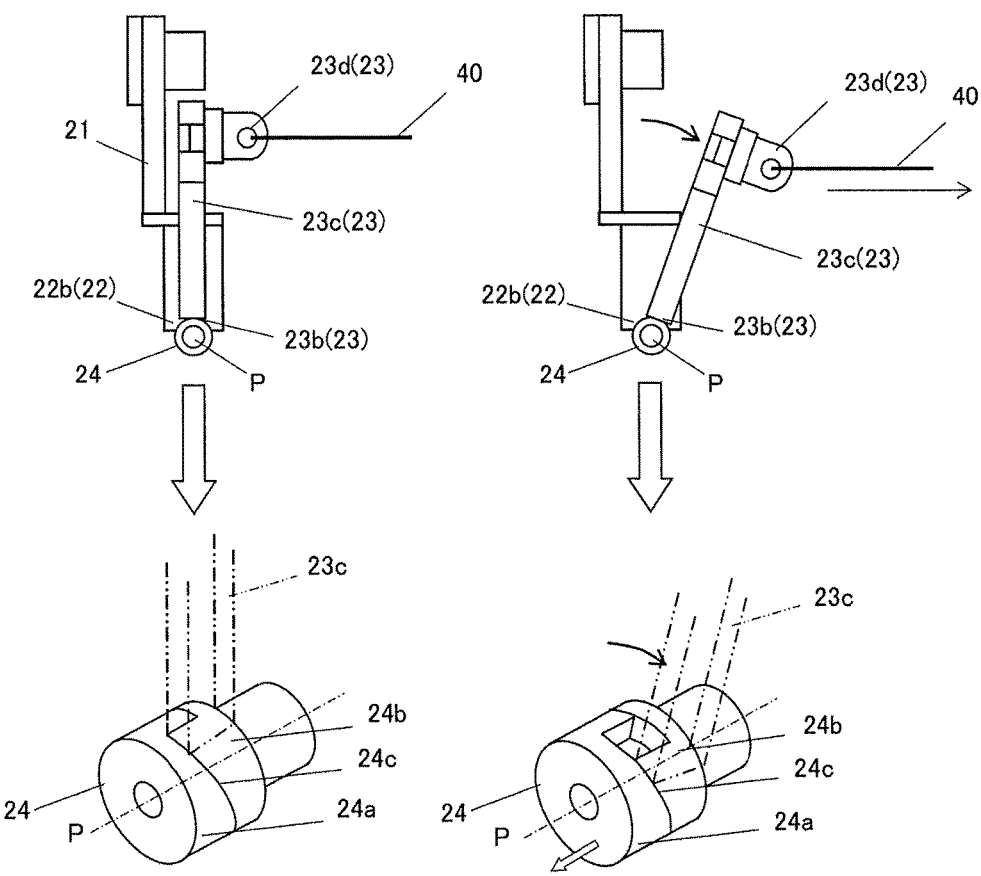
FIGS. 3(a) and 3(b) are diagrams illustrating an operation of a cam mechanism provided to the spigot-side supporting member.

As illustrated in FIGS. 3(*a*) and 3(*b*), when the arch-shaped member 23*c* is pivoted about the pivot axis P by pulling force of the pulling wire 40, the cam member 24*b* rotates relative to the cam member 24*a* along the inclined cam surface 24*c*. Thus, the cam member 24*a* is biased toward the pipe 3. The cam mechanism illustrated in FIGS. 3(*a*) and 3(*b*) is merely an example, and various known cam mechanisms can be employed to implement a similar function.

More specifically, the both end sections 23*a* and 23*b* of the arch-shaped member 23*c* function to press both lower end sections of the curved plates 22*a* and 22*b* of the spigot-side contact piece 22 toward the pipe 3, whereby the pipe 3 is clamped by the spigot-side contact piece 22. Preferably, the pivot axis P and the axis of the pipe 3 are set to be in an orthogonal positional relationship.

The pivoting member is not limited to the arch-shaped member 23*c* as in the present embodiment, as long as the cam member 24*a* can rotate, and may be a member having a "rectangular U" shape with a lower side open for example. When the arch-shaped member 23*c* is pivoted about the pivot axis P by the pulling force of the pulling wire 40, the annular member 23*d* comes into contact with the upper surface of the pipe 3. Thus, the clamping force applied to the pipe 3 from the spigot-side contact piece 22 is restricted, whereby no large force that deforms the pipe 3 is produced.

A similar function can be implemented with the inclined cam surface 24*c*, formed on the cam mechanism, having a sophisticated shape with which an inclined range of the inclined cam surface 24*c* is limited, when a certain level of clamping force is applied so that the cam member 24*b* can rotate relative to the cam member 24*a* with the pressing force kept at a constant level.

Figures 4A, 4B:
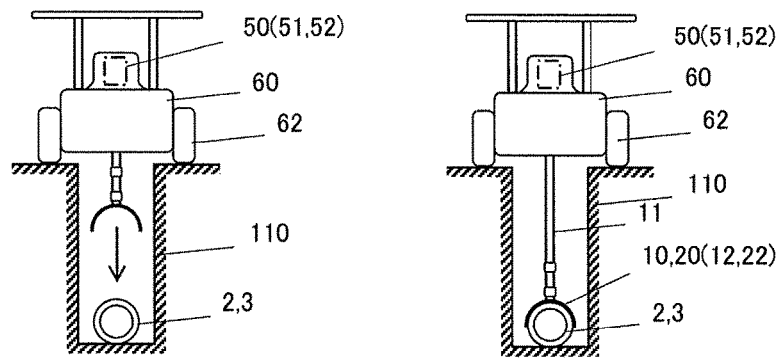
FIGS. 4(a) to 4(d) are diagrams illustrating a procedure of an assembling operation using the pipe joint assembling device according to the present invention.
Figure 4C:
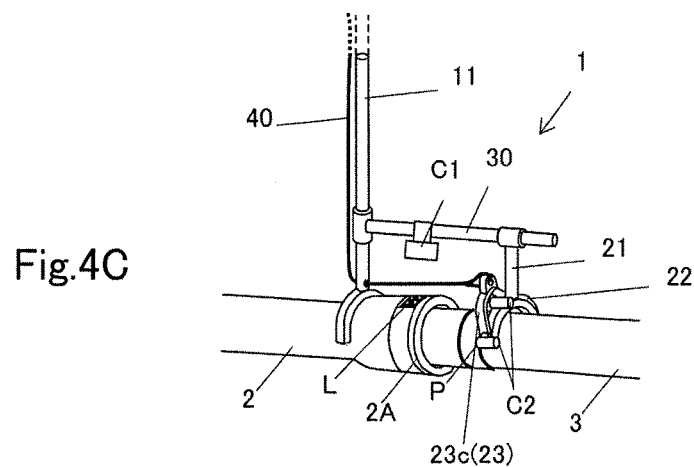
Figure 4D:
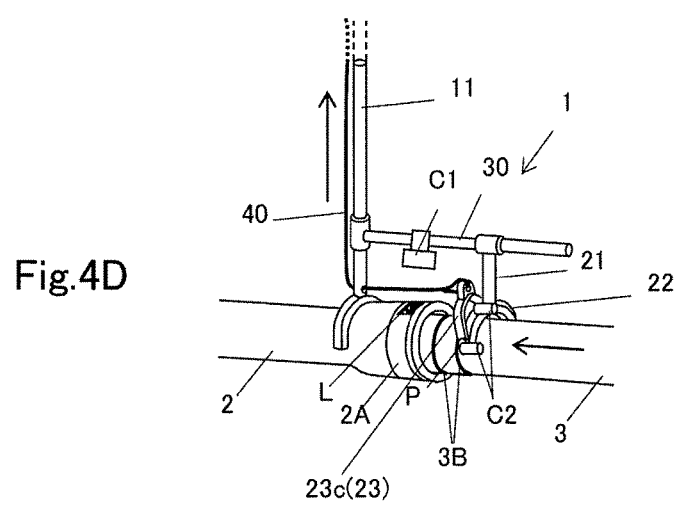

FIGS. 4(*a*) to 4(*d*) illustrate a procedure of assembling the pipes 2 and 3 with the pipe joint assembling device 1 described above. As illustrated in FIG. 4(*a*), first of all, the moving member 60 is moved to an assembling target position of the pipes 2 and 3, disposed on the trench bottom in a state where the socket of the one pipe 2 is receiving the spigot of the other pipe 3.

Next, as illustrated in FIG. 4(*b*), the elevation mechanism 51 is operated so that the socket-side supporting shaft 11 moves downward to make the socket-side contact piece 12 come into contact with a portion around the socket 2A from above to be fitted on the pipe circumferential surface. In this state, the spigot-side contact piece 22 of the spigot-side supporting member 20 comes into contact with a portion adjacent to the spigot 3A of the pipe 3 from above, to be fitted on the pipe circumferential surface.

As illustrated in FIG. 4(*c*), the winch mechanism 52 is started so that the pulling wire 40 performs the operation of pulling the arch-shaped member 23*c*, whereby the arch-shaped member 23*c* pivots about the pivot axis P. Thus, the pipe 3 is clamped by the spigot-side contact piece 22 through the operation of the cam mechanism 24.

As illustrated in FIG. 4(*d*), when the pulling wire 40 is pulled further in this state, the clamping force of the cam mechanism 24 increases. As a result, the spigot-side pipe 3, clamped by the spigot-side contact piece 22, is pulled toward the socket-side pipe 2, whereby the pipes are assembled.

Reaction force, applied to the socket-side contact piece 12 in this process, is received by a large diameter portion (step portion) extending from a center portion of the pipe 2 to a side of the socket 2*a*. The shape of the annular member of the pivoting mechanism 23 is illustrated simply in FIG. 4(*c*) for the sake of description and the like, and thus is structurally different from the annular member 23*d* illustrated in FIG. 1(*c*).

The spigot-side pipe 3 is pulled toward the socket-side pipe 2, with the spigot-side supporting member 20 sliding along the guide shaft 30, fixed to have the parallel position with respect to the axis of the socket-side pipe 2. Thus, even when a fitting or a short pipe is used, the spigot-side pipe 3 is prevented from inclining upward, whereby the pipes 2 and 3 are assembled with the inclination of the axes thereof kept within a predetermined allowable angle.

More specifically, the pipes 2 and 3 are assembled with a pipe joint contact method according to the present invention including: bringing a socket-side supporting member into contact with a socket-side pipe; bringing a spigot-side contact piece into contact with the spigot-side pipe; pulling a pulling operation member connected to a pivoting mechanism via a socket-side supporting member from the socket-side to make the pivoting mechanism pivot about a pivot axis so that the spigot-side contact piece is pressed and clamps the pipe; and pulling the spigot toward the socket in this clamped state.

An iron pipe has a larger diameter tolerance at a joint portion compared with cases where other pipe materials are used, and thus a seal member used therefor is set to have a larger compression allowance to ensure sealing performance after the assembling. Assembling with the joint for the iron pipes involves relatively large insertion resistance for compressing the seal member. Thus, the pipes are likely to have relative positions at the time of assembling changed to hinder the assembling.

Thus, the pipe to be inserted is likely to fall in a state of being incapable of being inserted with a rear end inclined in a direction to be deviated from an axis of the counterpart pipe. In particular, when the pipe to be inserted is short, the moment of lifting the rear end of the pipe upward due to the external force applied for the insertion is extremely larger than moment due to the own weight of the pipe. Thus, counter force that needs to be applied from the external to prevent the lifting is too large to be manually provided, and thus an extremely large scale device is required.

In view of the above, the guide shaft 30 described above is provided to receive the moment in the direction of lifting the rear end of the pipe upward. Thus, the pipes 2 and 3 can be smoothly assembled without having the axes thereof largely inclined. The guide shaft 30 may be provided as a single shaft or may be provided as a plurality of shafts to achieve high rigidity. For example, two shafts may be arranged in parallel to each other on both sides of the pipe, or two upper and lower shafts may be arranged in parallel to each other above the pipe.

Figure 5:
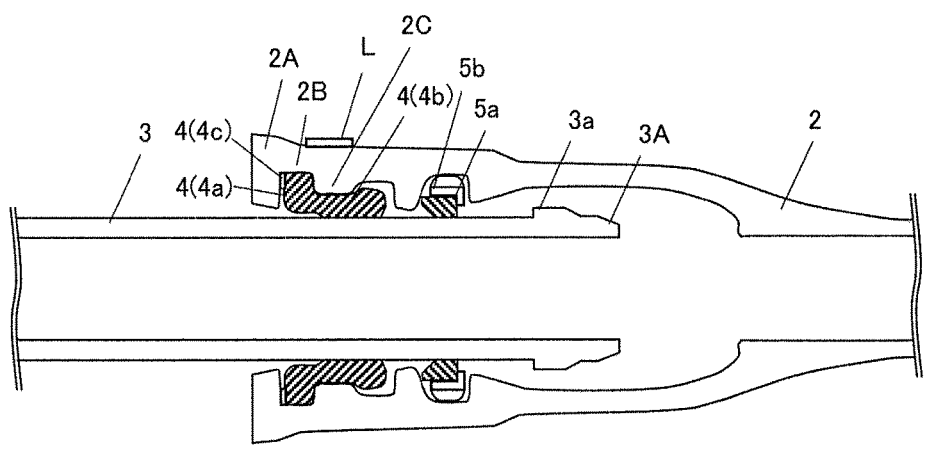
FIG. 5 is a cross-sectional view of a joint portion between pipes assembled with the pipe joint assembling device.

FIG. 5 illustrates a cross section of a joint section between the pipes 2 and 3 assembled with the pipe joint assembling device 1 described above. Into the socket 2A, formed in an end section of the one pipe 2, the spigot 3A, formed in an end section of the other pipe 3, is inserted. A rubber ring 4 (hereinafter, also referred to as "seal member 4") for sealing is provided and compressed between the inner circumferential surface of the socket 2A and the outer circumferential surface of the spigot 3A. A lock ring 5a and a protruding section 3a formed on the spigot 3A are engaged with each other to prevent the pipes from separating. In FIG. 5, a reference numeral 5b denotes a lock ring positioning member.

The pulling operation member 40 is not limited to the pulling wire that is a relatively light and simple mechanism, as in the example of the embodiment described above. Thus, a rack and pinion mechanism, a hydraulic jack mechanism, or the like may be employed as long as the operation of making the arch-shaped member 23c pivot can be performed.

In the embodiment described above, the pipe joint assembling device 1 is described in which the socket-side supporting member 10, the spigot-side supporting member 20, the guide shaft 30, and the pulling operation member 40 are supported by the supporting mechanism 50 provided to the moving member 60. However, the pipe joint assembling device 1 according to the present invention is not limited to the configuration where the components are mounted to the moving member 60. A configuration may be employed in which an operator holds and moves the socket-side supporting shaft 11 to a predetermined assembling portion, and performs a manual operation of pulling the pulling wire 40, as illustrated in FIG. 10(*a*).

Thus, the pipe joint assembling device 1 may have a configuration in which the socket-side supporting member 10 and the spigot-side supporting member 20 are manually moved downward to be in contact with the pipes 2 and 3, and then a lever 102a of a manual wind-up device such as a lever hoist 102 is operated so that the pulling wire 40 is wound up to join the pipes 2 and 3.

Figure 11A:
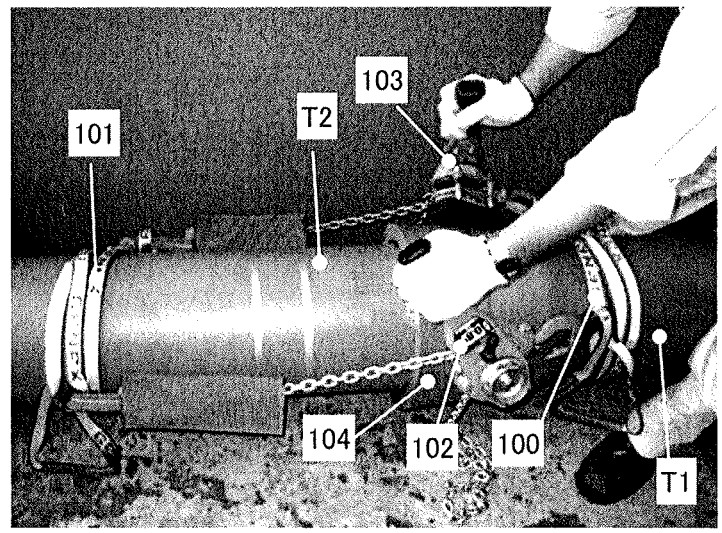
FIG. 11(a) is a photograph illustrating a conventional assembling operation.
Figure 11B:
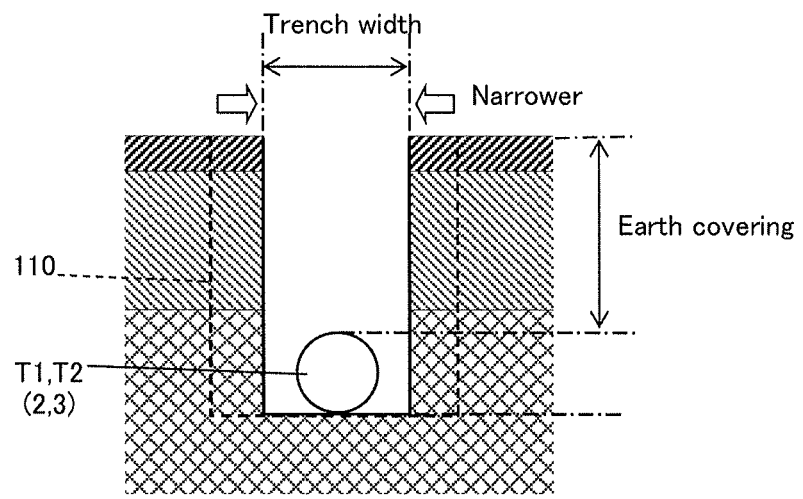
FIG. 11(b) is a diagram illustrating a comparison between a trench shape corresponding to the conventional assembling operation and a trench shape corresponding to a assembling operation using the pipe joint assembling device according to the present invention.

By using the pipe joint assembling device 1 with such a configuration, as illustrated in FIG. 11(*b*), the socket-side contact piece and the spigot-side contact piece are moved downward from above the pipes 2 and 3 disposed on the trench bottom of the excavated trench 110 to be respectively in contact with the pipes 2 and 3 and fitted on the circumferential surfaces. Then, the assembling operation is completed only by operating the pulling operation member, whereby the operator needs not to enter the trench to perform the operation. Thus, the trench excavated can have a small width.

A pipeline construction management information collecting system according to the present invention collects pipeline construction management information at a construction site for the pipeline construction described above.

Figure 6:
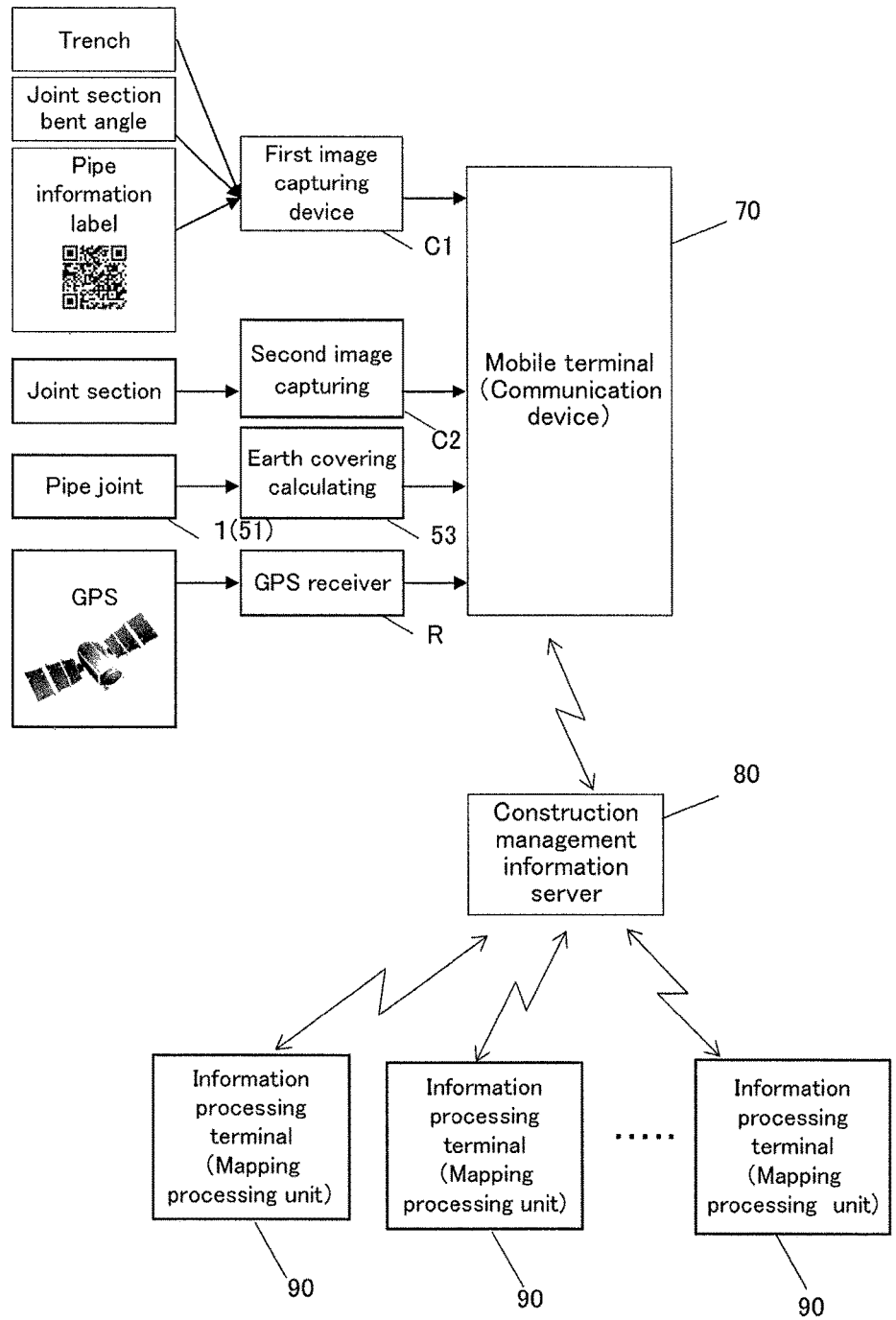
FIG. 6 is a diagram illustrating a drawing support system for as-built drawing of pipeline.

As illustrated in FIG. 6, the pipeline construction management information collecting system includes the pipe joint assembling device 1 that acquires the construction management information, the image capturing devices C1 and C2, the GPS receiver R, and a communication device 70.

The image capturing devices C1 and C2 are attached to the pipe joint assembling device 1 and are configured to read the construction management information. The GPS receiver R serves as a position information acquisition device that acquires position information of the assembling section of the pipes assembled with the pipe joint assembling device 1.

The communication device 70 is configured to transmit to a construction management information server 80 serving as a construction information management device, the construction management information acquired by the pipe joint assembling device 1, the construction management information acquired by the image capturing devices C1 and C2, and the position information acquired by the position information acquisition device R.

The image capturing devices include: a first image capturing unit C1 that captures images of the trench excavated when the pipes 2 and 3 are laid, the pipe information label attached on the pipe, and a deflection angle of the pipe after the assembling, from above; and a second image capturing unit C2 that captures an image of the seal member 60 at the assembling section between the pipes 2 and 3 from the spigot-side.

A mobile terminal that can perform wireless communications is used as the communication device 70, and a mobile phone or a smartphone is preferably used for example. For example, the depth of cover calculating unit 53 of the pipe joint assembling device 1, the image capturing devices C1 and C2, and the position information acquisition device R are provided with a short-range communication unit supporting Bluetooth (registered trademark) standard for example, and thus are configured to be capable of transmitting and receiving data to and from a mobile terminal 70 including a short-range communication unit also supporting Bluetooth (registered trademark) standard.

When the moving member 60 is moved to the assembling target position for the pipes 2 and 3 as illustrated in FIG. 4(*a*), the first image capturing device C1 captures an image of the trench 110 from the trench upper side and the position information acquisition device R receives latitude and longitude serving as the position information of the assembling section, before the elevation mechanism 51 moves the assembling processing unit 10, 20, 30, 40 downward.

When the elevation mechanism 51 moves the assembling processing unit 10, 20, 30, 40 downward until the socket-side contact piece 12 comes into contact with the pipe as illustrated in FIG. 4(*b*), for example, the depth of cover calculating unit 53 measures the number of rotations of the pinion gear and converts the number of rotations into a downward movement distance, and calculates depth of cover information while taking an initial height of the assembling processing unit, with the ground surface serving as a reference, into consideration.

Before the pulling wire 40 performs the operation of pulling the arch-shaped member 23c as illustrated in FIG. 4(*c*), the first image capturing device C1 captures an image of the two-dimensional code information on the pipe information label L attached to the surface of the socket-side pipe.

When the pipes 2 and 3 are assembled as illustrated in FIG. 4(*d*), the first image capturing device C1 captures an image of the assembling section with a white line 3B painted on the surface of the pipe 3 at the portion, adjacent to the socket 2A and the spigot 3A, included within an angle of view. The second image capturing device C2, attached to the socket-side contact piece 12, captures an image of the seal member 4 on the inner side of the socket 2A.

The timing of the reception by the position information acquisition device R, the timing of the vertical movement caused by the elevation mechanism 51, and the timing of the image capturing performed by the image capturing devices C1 and C2 are controlled through the short-range communication unit with an application program, installed in the mobile terminal 70, operating in accordance with an operation performed by an operator on a screen of the mobile terminal 70.

Similarly, the depth of cover information that is the construction management information calculated by the depth of cover calculating unit 53, the image information from the image capturing devices C1 and C2, the position information received by the position information acquisition device R are obtained by the mobile terminal 70 through the short-range communication unit in accordance with an operation performed by the operator on the screen of the mobile terminal 70.

In the mobile terminal 70, predetermined image processing program starts for an image of the opening section of the trench transmitted from the first image capturing device C1 so that the trench width is calculated, the deflection angle of the pipes, after the assembling, on a horizontal plane is calculated from the image of the white line at the assembling section, and pipe information corresponding to the two-dimensional code information is searched in a pipe information database stored in a memory of the mobile terminal 70. The pipe information includes a manufacturing date, a manufacturing plant, a model, a pipe type, a nominal diameter, a serial number of the pipe, and the like.

Instead of capturing the image of the pipe information label L attached to the pipe, the code information carved on the pipe, the code information painted on the pipe, and the like, by the first image capturing device C1, the pipe information may be acquired by employing an RF-ID technique with an IC tag, storing the pipe information, mounted to the pipe and an IC tag reader mounted to the pipe joint assembling device 1.

Figure 9A:
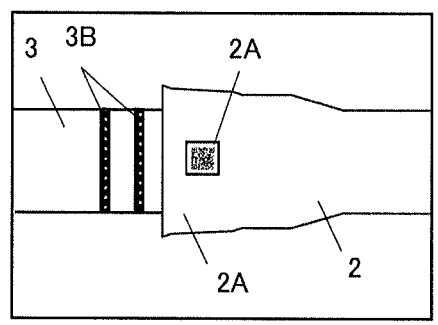
FIG. 9 is a diagram illustrating how a pipe deflection angle is measured.
Figure 9B:
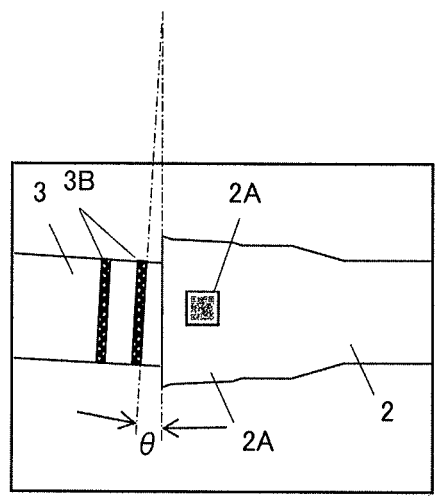

FIGS. 9(a) and 9(b) each illustrate an example of the image of the white line at the assembling section. FIG. 9(a) illustrates a state where the pipes are substantially linearly assembled, and FIG. 9(b) illustrates a condition where the pipes are assembled while being slightly deflected. In the image processing, executed in the mobile terminal 70, a linear end section edge of the socket-side pipe 2 and a longitudinal direction edge of the white line 3B are extracted as linear images, an inclined angle between a reference and each of the linear images is obtained, and a deflection angle θ is obtained by calculating the difference between the inclined angles.

The seal member 4, transmitted from the second image capturing device C2, is displayed on the screen of the mobile terminal 70, and when the operator visually checks the image and determines that there is no abnormality, the operator proceeds to the assembling operation for the next pipe.

The depth of cover information, the pipe information, the position information, and the image information, which are the construction management information collected by the mobile terminal 70, are transmitted to the construction management information server 80 at a remote location through a wireless LAN such as a wireless Wi-Fi. A communication medium for transmitting these pieces of construction information is not limited to the wireless LAN, and other wireless communication media, such as a mobile phone line or a satellite communication line, may be used as appropriate.

Thus, the pipeline construction management information collecting method of collecting the construction management information for the piping at the construction site for the pipeline construction is executed by the pipe joint joining device 1, the image capturing devices C1 and C2, the GPS receiver R, and the mobile terminal 70.

More specifically, the pipeline construction management information collecting method includes: an arranging step of arranging a pipe joint assembling device above a assembling position of piping; a construction position information acquiring step of acquiring position information of the pipe joint assembling device with a GPS receiver; a trench width information acquiring step of capturing an image of a trench width of an excavated trench from above by an image capturing device attached to the pipe joint assembling device and automatically calculating the trench width from the captured image; a depth of cover information acquiring step of remotely operating an elevation mechanism so that the assembling processing unit is moved downward to the assembling position of the piping, and automatically calculating depth of cover from a distance of the downward movement; and a pipe information acquiring step of capturing an image of a pipe information label attached to a socket-side pipe with an image capturing device attached to the pipe joint assembling device and automatically acquiring pipe information from the captured image.

The method further includes: an assembling step of remotely controlling the assembling processing unit so that the joint section of the piping is assembled; a deflection angle information acquiring step of capturing an image of the pipe joint section after the assembling from above with the image capturing device and automatically calculating a deflection angle of the piping from the captured image; a seal state information image capturing step of capturing an image of a seal member at the assembling section from a spigot side with the image capturing device; and a construction information transmitting step of transmitting the construction position information, the trench width information, the depth of cover information, the pipe information, the deflection angle information, and the seal state information, acquired in the steps, to a construction information management device with a communication device.

Of the steps in the pipeline construction management information collecting method, the trench width information acquiring step, the depth of cover information acquiring step, the deflection angle information acquiring step, and the seal state information image capturing step are not essential steps, and one or a plurality of these steps may be employed as appropriate to be combined in the pipeline construction management information collecting method.

Next, assembled condition state management device and management method for the pipe joint are described.

Figure 8A:
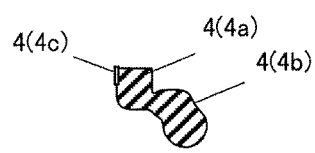
FIG. 8 is a diagram illustrating an assembled condition management method for the pipe joint.
Figure 8B:
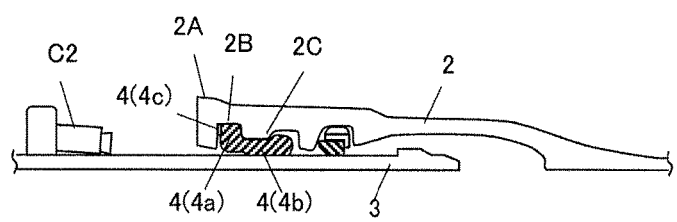

As illustrated in FIGS. 5, 8(a), and 8(b), the seal member (rubber ring) 4 includes a heel section 4a and a bulb section 4b. A colored marker member 4c is provided to a pipe inner surface side of a pipe end section side surface of the heel section 4a. In the condition where the pipes 2 and 3 are properly assembled, the seal member 4 has the heel section 4a fitted to the seal member accommodating recessed section 2B formed in the inner circumferential section of the socket 2A, and the bulb section 4b compressed between a seal member compressing protruding section 2C, coupled to the seal member accommodating recessed section 2B and the outer circumferential surface of the spigot-side pipe 3.

The assembled condition management device includes: the spigot-side contact piece 22 described above; and the second image capturing devices C2 that are attached to the spigot-side contact piece 22 and serve as an inspection device that performs contactless inspection on a circumferential section of the socket 2A along the axial direction of the pipe from the spigot-side pipe surface. Four second image capturing devices C2 are disposed along the circumferential surface of the pipe at a substantially equal interval (see FIG. 2(b)).

Figure 8C:
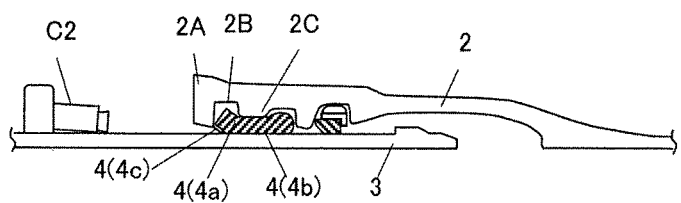

FIG. 8(b) illustrates a condition where the pipes 2 and 3 are assembled with appropriate position of the seal member 4, and FIG. 8(c) illustrates a condition where the pipes 2 and 3 are assembled with inappropriate position of the seal member 4 so that the bulb section 4b is pulled in by the pipe 3 and thus the heel section 4a is separated from the seal member accommodating recessed section 2B.

When the assembling operation for the pipes results in the inappropriate condition illustrated in FIG. 8(c), a sealing function is deteriorated, and thus the assembling operation needs to be redone. In a conventional case, when the assembling operation is completed, the operator enters the trench to check the position of the seal member 4 by using a gap gauge and the like. With the assembled condition management devices 22 and C2 described above, such a cumbersome operation is no longer required.

The image captured by the second image capturing device C2 is transmitted to the mobile terminal 70 (see FIG. 6), and can be checked on the screen of the mobile terminal 70. For this purpose, the colored marker member 4c is provided to the heel section 4a. The assembled condition can be evaluated based on whether the marker member 4c, provided to the socket-side end surface of the heel section 4a, is detected by an inspection device.

Figure 8D:
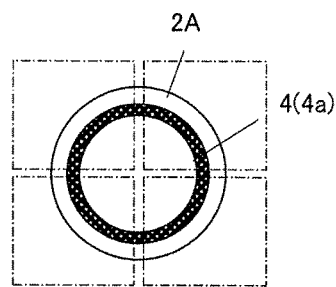

FIG. 8(d) illustrates an image corresponding to FIG. 8(b) illustrating assembling in the appropriate condition. The image includes no image corresponding to the marker member 4c provided to the heel section 4a, and thus it can be determined that the appropriate assembling has been achieved.

Figure 8E:
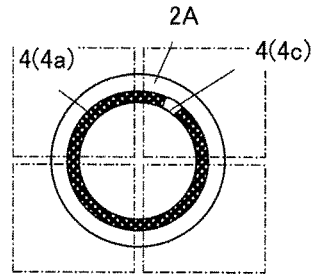

FIG. 8(e) illustrates an image corresponding to FIG. 8(c) illustrating assembling in the inappropriate condition. The image includes the image corresponding to the marker member 4c at the upper right of the heel section 4a, and thus it can be determined that the assembling is inappropriate. Areas illustrated with one dot chained lines in the figure represent ranges of image capturing by the four second image capturing devices C2. The image capturing ranges adjacent to each other are preferably set to partially overlap with each other so that the evaluation over the entire area can be ensured.

The configuration in which the marker member 4c is a colored member having a color different from a color of the seal member 4, and the inspection device is the image capturing device with which whether there is the colored member can be determined with an image, can be easily implemented. However, the configuration is not necessarily limited to that in which the marker member 4c is the colored member. Furthermore, the second image capturing device C2 does not necessarily be a normal image capturing device using visible light.

Figure 8F:
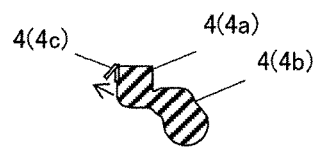

For example, any marker member may be employed as long as the separation of the heel section 4a from the seal member accommodating recessed section 2B can be checked. As illustrated in FIG. 8(f), a blade-shaped marker member 4c may be employed that is in contact with the heel section 4a while fitting around the heel section 4a in a condition where the heel section 4a is accommodated in the seal member accommodating recessed section 2B, and is partially lifted from the heel section 4a in a condition where the heel section 4a is separated from the seal member accommodating recessed section 2B.

For example, the marker member 4c may be formed of a fluorescent member, and the inspection device may be a sensor that can detect fluorescent light. A light reflecting member may be used with which reflected light corresponding to a predetermined wavelength of light emitted onto the seal member in the socket-side from the spigot-side pipe can be detected.

The portion where the colored marker member 4c is provided is not limited to the inner surface side of the pipe in the pipe end section side surface of the heel section 4a, and may be any portion with which the condition where the heel section 4a is separated from the seal member accommodating recessed section 2B can be detected. Thus, any seal member may be used in which the heel section, fitted in the recessed section formed in the inner circumferential section of the socket, is provided with the marker member with which the separation of the heel section from the recessed section can be detected.

In the example described above, the configuration is described in which the bulb section 4b of the seal member is compressed between the seal member compressing protruding section 2C, coupled to the seal member accommodating recessed section 2B, and the outer circumferential surface of the spigot-side pipe 3. However, the seal member compressing protruding section 2C is not necessarily formed on the inner circumference of the socket-side pipe. A configuration may be employed in which the bulb section 4b is compressed between the inner circumferential surface of the socket and the outer circumferential surface of the spigot.

Thus, a pipe joint structure may be employed in which a spigot that is formed at an end of one pipes to be assembled is inserted into a socket that is formed at an end of another pipe, a seal member is provided between the socket and the spigot, the seal member includes a heel section fitted to a recessed section formed in an inner circumferential section of the socket and a bulb section compressed between an inner circumferential surface of the socket and an outer circumferential surface of the spigot, and the heel section accommodated in the recessed section is provided with a marker member.

The second image capturing device C2 may be used in the following manner. Specifically, instead of providing the plurality of second image capturing devices C2 on the spigot-side contact piece 22, a single second image capturing device C2 may be attached via a movement mechanism, including a rail, a driving unit, and the like that moves the second image capturing device C2 along the pipe circumferential surface on the socket-side. In this case, the second image capturing device C2 may perform image capturing after being moved to a predetermined position by the movement device, or capture a moving image while moving.

The assembled condition management device preferably includes the spigot-side contact piece 22 provided to the pipe joint assembling device 1. However, the configuration is not necessarily limited to this. For example, a spigot-side contact piece that is moved downward from above the excavated trench by a manual operation of the operator to be in contact with the pipe surface of the spigot-side from above to fit on the pipe surface may be prepared, and an image capturing device may be attached to the spigot-side contact piece.

Furthermore, the assembled condition management device may have the following configuration. Specifically, a light source that emits light to the seal member from the socket side and a mirror that reflects reflected light from the seal member to an observer may be provided to the spigot-side contact piece, so that the whether the marker member is observed is determined based on the reflected light reflected from the mirror.

Next, a drawing support system for as-built drawing of pipeline that produces as-built drawing of pipeline based on the construction management information transmitted to the construction management information server 80 described above is described with reference to FIG. 6.

The drawing support system for as-built drawing of pipeline includes: a pipe information acquisition device that acquires the pipe information; a GPS receiver that acquires the position information; an image acquisition device that acquires an image of the joint portion; a construction management information server 80 to which the pipe information, the position information, and the image information are uploaded; and a plurality of information processing terminals 90 that produce the as-built drawing of pipeline based on the pipe information, the position information, and the image information downloaded from the construction management information server 80. Preferably, the construction management information server 80 is a cloud server.

The depth of cover information and the trench width information may be further uploaded to the construction management information server 80 so that an offset diagram indicating a buried position of the pipes more accurately than the as-built drawing can be produced by the information processing terminals 90. In such a case, the depth of cover information and the trench width information may be uploaded from the mobile terminal 70 described above.

The pipe information acquisition device acquires the pipe information, based on captured image information of the pipe information label L attached to a pipe disposed in the construction site, and may include the first image capturing device 1C and the mobile terminal 70 described above.

The GPS receiver includes the GPS receiver R mounted to the moving member 60 described above, and the image acquisition device includes the image capturing devices C1 and C2 described above. With the mobile terminal 70, the pipe information, the position information, and the image information are uploaded to the construction management information server 80 from the construction site.

A predetermined right to access the construction management information server 80 is set to the information processing terminal 90, and thus, an operator having the access right can connect to the construction management information server 80.

The information processing terminal 90 includes a mobile terminal and the like such as a personal computer, a tablet computer, or a smartphone. In the information processing terminal 90, mapping software for producing the as-built drawing is installed, and cooperates with hardware of the information processing terminal 90 to function as a mapping processing unit.

The mapping processing unit produces the as-built drawing by drawing a symbol representing the pipe joint at a construction position in a reference coordinate system that is a virtual plane linked with an actual map information, based on the pipe information downloaded from the construction management information server 80, and connecting between the pipe joints, at the construction positions, with a shape corresponding to the pipe type.

Figure 7:
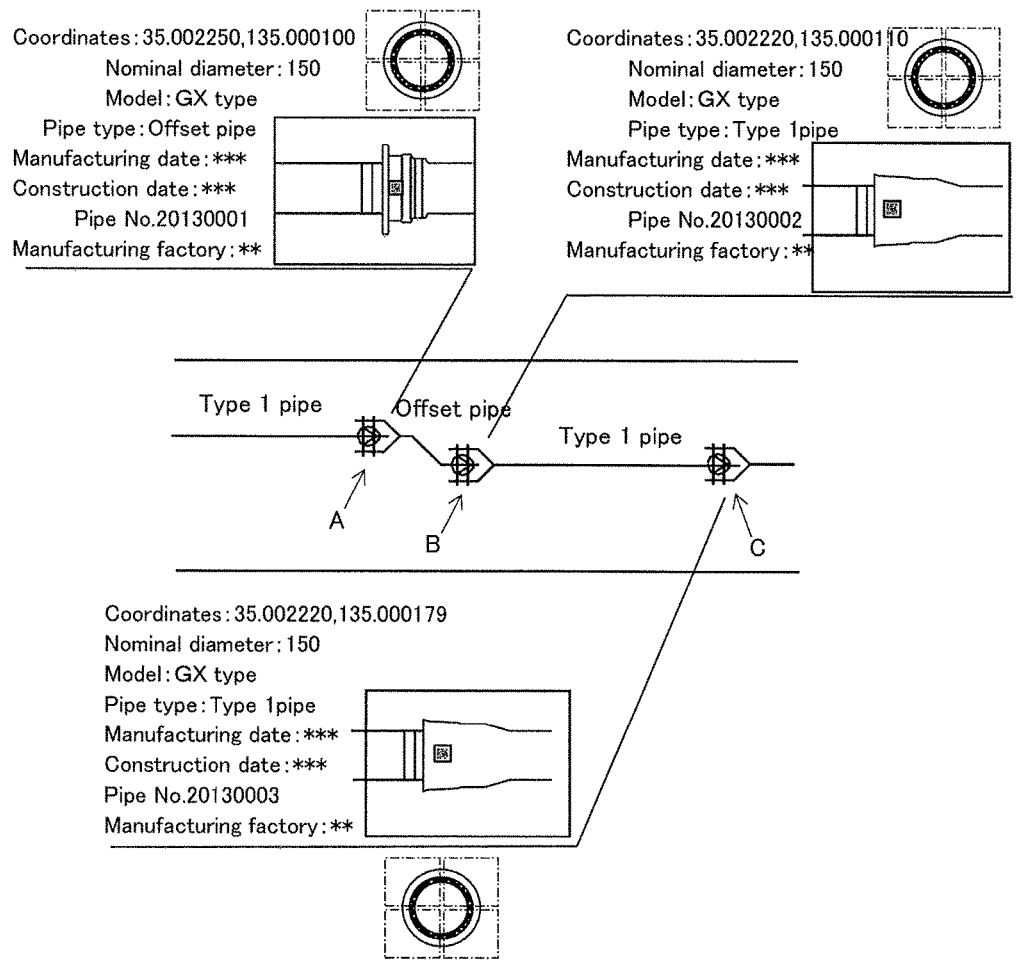
FIG. 7 is a diagram illustrating an as-built drawing with the drawing support system for as-built drawing of pipeline.

FIG. 7 illustrates an example of an as-built drawing produced by the mapping processing unit. The mapping processing unit first plots construction position (longitude and latitude) points A, B, and C obtained by the GPS receiver, and links the pipe information and the captured image with each point.

Then, the symbol of the pipe joint is drawn at each plotted point, and then the shape corresponding to the pipe type is drawn between the symbols. The as-built drawing can be produced by sequential drawing based on an operation input from the operator, and may be automatically produced based on the construction positions as well as the pipe information and the captured images linked to the construction positions.

In FIG. 7, symbols of GX type pipe joints are connected to each other with shapes corresponding to a class-1 thickness pipe and an offset pipe. The offset pipe is one of fittings, and the fittings further include a bend, a tee, a short pipe, a cross pipe, and the like for which corresponding shapes are respectively set.

The as-built drawing, produced by the mapping processing unit, may be produced on the hardware of the information processing terminal 90 and uploaded to the construction management information server 80, or may be drawn by the hardware of the information processing terminal 90 and produced on the hardware of the construction management information server 80 of a cloud type.

In the latter case, no standalone mapping software with a large capacity needs to be installed in the information processing terminal 90, and only interface software for cloud operation needs to be installed. Thus, a large memory capacity is not required.

When the depth of cover information and the trench width information are further uploaded to the construction management information server 80, the mapping processing unit may automatically produce the offset diagram further taking the depth of cover information and the trench width information into consideration.

Thus, an as-built drawing of pipeline producing method of collecting construction management information of pipeline at a construction site for pipeline construction to produce an as-built drawing of pipeline includes: uploading pipe information, position information, and image information, obtained by a pipe information acquisition device that acquires the pipe information based on captured image information of a pipe information label attached to a pipe disposed in the construction site, a GPS receiver that acquires position information of the construction site, and an image acquisition device that acquires an image of an assembled joint section, to a construction management information server with a transmission device; and producing the as-built drawing of pipeline on a map managed by a mapping processing unit provided in an information processing terminal, based on the pipe information, the position information, and the image information downloaded from the construction management information server to the information processing terminal.

The pipe information acquisition device, the GPS receiver, and the image acquisition device are combined with the pipe joint assembling device 1 described above. The pipeline construction supporting software is installed in the mobile terminal 70 described above. An operation screen, based on the pipeline construction software, is displayed on the screen of the mobile terminal 70. The operator only needs to operate the operation screen on the mobile terminal 70, after pulling the moving member 60 of the pipe joint assembling device 1 to be positioned at the construction position for automatically conducting the assembling operation. The construction position information, the trench width information, the depth of cover information, the pipe information, the deflection angle information, the seal condition information, and the like can be automatically collected, and automatically transmitted to the construction information management device with the communication device.

More specifically, an operation screen, corresponding to a construction procedure, is displayed on the screen of the mobile terminal 70, and information required for each operation is automatically connected in the mobile terminal 70. A construction position information acquisition instruction screen, a trench width measurement instruction screen, a depth of cover information acquisition instruction screen, a pipe information acquisition instruction screen, a deflection angle information acquisition instruction screen, a seal condition information acquisition instruction screen, and an information transmission instruction screen are displayed in this order. When the operator touches an operation icon on each screen, an information acquisition instruction is transmitted to a corresponding unit through the short-range communication unit. Then, corresponding information transmitted from the corresponding unit in response to is used for performing required calculation processing, whereby the trench width information, the depth of cover information, the pipe information, and the like are automatically generated. Then, when the operator touches an operation icon on the information transmission instruction screen, required information is automatically transmitted to the construction information management device.

An image processing program that automatically determines whether the image includes the image of the marker member, based on an image serving as the seal condition information transmitted from the second image capturing device C2 may be installed in the mobile terminal 70, and determination result information indicating whether the sealing condition is appropriate may be displayed. In this case, when the result indicating the appropriate condition is not displayed, an instruction for automatic transmission to the construction information management device may be denied.

For example, an operation on the screen of the mobile terminal 70 may initiate a series of operations described above including: capturing the image of the trench width; processing of moving the assembling processing unit 10, 20, 30, 40 downward; the measurement of the depth of cover information; capturing of the image of the information label L; automatic winding up of the pulling wire 40; capturing of the image of the joint section after the assembling; and the like.

More specifically, a control program, with which the elevation mechanism 51 and the winch mechanism 52 of the pipe joint assembling device 1 can be remotely operated may be installed in the mobile terminal 70, and cooperate with the program that collects the construction information and the like described above. For example, when an operation icon on the depth of cover information acquisition instruction screen described above is operated, the elevation mechanism 51 is started to move the assembling processing unit downward. After the pipe information acquisition instruction screen is operated and the pipe information is acquired, an assembling processing start instruction screen is displayed. When an operation icon on this screen is operated, the winch mechanism 52 is started. In this manner, control interlocked with the pipe joint assembling device 1 can be achieved.

The embodiment described above is merely one embodiment of the present invention, and thus the content thereof does not limit the scope of the present invention. A specific shape, size, material, configuration, and the like of each component can be designed differently as appropriate, as long as the advantageous effects of the present invention can be obtained.

DESCRIPTION OF SYMBOLS

1: pipe joint assembling device
2: pipe
2A: socket
3: pipe
3B: spigot
10: socket-side supporting member
12: socket-side contact piece
20: spigot-side supporting member
22: spigot-side contact piece
23: pivoting mechanism
24: cam mechanism
30: guide shaft
40: pulling operation member (pulling wire)
53: depth of cover calculating unit
70: mobile terminal (communication device)
80: construction management information server
90: information processing terminal (mapping processing unit)
C1: first image capturing device
C2: second image capturing device
R: GPS receiver

The invention claimed is:

1. An assembled condition management method for a pipe joint in which a spigot that is formed in an end section of one of pipes to be joined is inserted into a socket that is formed in an end section of another one of the pipes, and a seal member is provided between the socket and the spigot, the seal member including: a heel section that is fitted to a recessed section formed in an inner circumferential section of the socket; and a bulb section that is compressed between an inner circumferential surface of the socket and an outer circumferential surface of the spigot, the heel section that is accommodated in the recessed section being provided with a marker member, the method comprising:
   checking the marker member in a non-contact manner from a side of the spigot along a pipe axial direction in a state where the pipe joint is assembled.

2. An assembled condition management device in combination with a pipe joint in which a spigot that is formed at an end of one pipe to be joined is inserted into a socket that is formed at an end of another pipe, and a seal member is provided between the socket and the spigot, the seal member including: a heel section that is fitted to a recessed section formed in an inner circumferential section of the socket; and a bulb section that is compressed between an inner circumferential surface of the socket and an outer circumferential surface of the spigot, the heel section accommodated in the recessed section being provided with a marker member,
   for the seal member, the assembled condition management device comprising:
   a marker detection device configured to be joined with the pipe joint such that when joined, the marker detection device is configured to detect the marker member from the spigot-side pipe along an axial direction of the pipe in a non-contact manner.

3. The assembled condition management device according to claim 2, wherein the marker member is a colored member having a color different from a color of the seal member, and the marker detection device includes an image capturing device with which whether there is the colored member is able to be determined with an image.

4. The assembled condition management device according to claim 3, wherein a spigot-side contact piece that comes into contact with a spigot side pipe, and the image capturing device is attached to the spigot-side contact piece, and wherein the image capturing device is attached to the spigot-side contact piece via a movement mechanism that moves along the spigot-side outer circumferential surface.

* * * * *